(12) United States Patent
Gharpure et al.

(10) Patent No.: US 11,192,848 B2
(45) Date of Patent: Dec. 7, 2021

(54) PROCESS FOR THE PREPARATION OF DROXIDOPA AND ITS INTERMEDIATE

(71) Applicant: PIRAMAL PHARMA LIMITED, Mumbai (IN)

(72) Inventors: Milind Gharpure, Maharashtra (IN); Ashutosh Jagtap, Maharashtra (IN); Changdev Raut, Maharashtra (IN); Navnath Patil, Maharashtra (IN); Prashant Ladkat, Maharashtra (IN); Jaisankar Krishnapillai, Maharashtra (IN); Nirmal Kumar Manoharan, Maharashtra (IN); Kumaravel Kandasamy, Maharashtra (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 0 days.

(21) Appl. No.: 16/959,332

(22) PCT Filed: Jan. 3, 2019

(86) PCT No.: PCT/IB2019/050048
§ 371 (c)(1),
(2) Date: Jun. 30, 2020

(87) PCT Pub. No.: WO2019/135189
PCT Pub. Date: Jul. 11, 2019

(65) Prior Publication Data
US 2020/0354308 A1   Nov. 12, 2020

(30) Foreign Application Priority Data
Jan. 4, 2018  (IN) .............................. 201821000399

(51) Int. Cl.
*C07C 227/40* (2006.01)
*C07D 207/16* (2006.01)
*C07C 229/36* (2006.01)

(52) U.S. Cl.
CPC .......... *C07C 227/40* (2013.01); *C07D 207/16* (2013.01); *C07B 2200/07* (2013.01); *C07C 229/36* (2013.01)

(58) Field of Classification Search
None
See application file for complete search history.

(56) References Cited

FOREIGN PATENT DOCUMENTS

| SU | 1189859 A1 | * | 11/1985 | ........... C07D 207/16 |
|----|------------|---|---------|------------------------|
| WO | 2013/167998 A | | 11/2013 | |
| WO | 2017/168313 A | | 10/2017 | |

OTHER PUBLICATIONS

Belokon et al., English language CAS SciFinder abstract of SU 1189859 A1 (Nov. 7, 1985).*
ISR for International Application No. PCT/IB2019/050048.
Written Opinion for International Application No. PCT/IB2019/050048.
Qin, W. et al., "Asymmetric synthesis of D- and L-serine with "Glycine (equivalent)" method", Huaxue Shiji=Chemical Reagents, (20050000), vol. 27, No. 11, doi:10.13822/j.cnki.hxsj.2005.11.002, pp. 643-640, 670, XP009521157 [A] 1-9 * see abstract and scheme on p. 643 *.
Deng, G. et al., "Synthesis of (S)-, (R)-, and (rac)-2-amino-3,3-bis(4-fluorophenyl) propanoic acids and an evaluation of the OPP IV inhibitory activity of Denagliptin diastereomers", Tetrahedron, (20080000), vol. 64, doi: 10.1016/j.tet.2008.08.097, pp. 10512-10516, XP025472236 [A] 1-9 * see title and Scheme 1 *.

* cited by examiner

*Primary Examiner* — Brian J Davis
(74) *Attorney, Agent, or Firm* — Ladas & Parry LLP

(57) ABSTRACT

The present invention provides an improved process for preparation of the L-threo-(2S,3R)-3-(3 4-dihydroxyphenyl)serine (I) or a salt thereof, which is known as Droxidopa; comprising (a) recovery of the by-product compound (V) (as described herein) from the crude compound (I), and (b) recycling and re-use it for the preparation of droxidopa. Accordingly, the present invention relates to an improved economical process for the preparation of L-threo-(2S,3R)-3-(3.4-dihydroxyphenyl)serine (I) or its pharmaceutically acceptable salts; wherein the process relates to recovery and recycling of the by-product compound (V) and also to re-use it for the preparation of droxidopa.

8 Claims, No Drawings

PROCESS FOR THE PREPARATION OF DROXIDOPA AND ITS INTERMEDIATE

RELATED APPLICATION

This application is an application under 35 U.S.C. 371 of International Application No. PCT/IB2019/050048 filed on 3 Jan. 2019, which claims priority from Indian Application No. 201821000399 filed 4 Jan. 2018, the disclosures of which are incorporated in their entirety by reference herein.

FIELD OF THE INVENTION

The present invention relates to an improved economical process for the preparation of L-threo-(2S,3R)-3-(3,4-dihydroxyphenyl)serine (I), which is known as Droxidopa and its pharmaceutically acceptable salts wherein the process relates to recovery and recycling of the by-product compound (V) and also to re-use it for the preparation of droxidopa.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Droxidopa is chemically known as (2S,3R)-2-amino-3-(3,4-dihydroxyphenyl)-3-hydroxypropanoic acid and it is structurally represented by the following formula (I). It is also 20 known as L-threo-(2S,3R)-3-(3,4-dihydroxyphenyl)serine. Droxidopa is available in the market as Northera® capsules with dosages of 100 mg, 200 mg and 300 mg for oral administration.

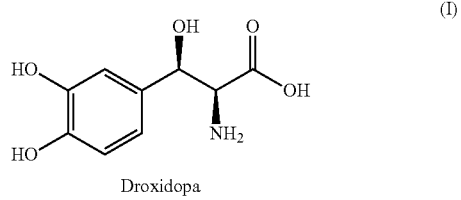 [SMILES: N[C@H](C(=O)O)[C@H](O)c1ccc(O)c(O)c1]

Droxidopa (I)

NORTHERA® (droxidopa) capsules, for oral use is approved in the USA and is indicated for the treatment of orthostatic dizziness, light headedness, or the "feeling that you are about to black out" in adult patients with symptomatic neurogenic orthostatic hypotension caused by primary autonomic failure, dopamine beta-hydroxylase deficiency, and non-diabetic autonomic neuropathy. Droxidopa is a synthetic amino acid analog that is directly metabolized to norepinephrine by dopadecarboxylase, which is extensively distributed throughout the body. The drug was originally launched in 1989 in Japan by Sumitomo Dainippon Pharma for the oral treatment of frozen gait or dizziness associated with Parkinson's disease and for the treatment of orthostatic hypotension, syncope or dizziness associated with Shy-Drager syndrome and familial amyloidotic polyneuropathy.

Chirality has acquired increasing importance for the pharmaceutical industry, as evidenced by the fact that more than 80% of the drugs developed hitherto have chiral properties.

The various enantiomers may develop completely different effects in the body, so that only one of two or more enantiomeric forms administered may be effective. In the case of Droxidopa (I), it has been observed that the L-threo enantiomer is the desired isomer having desired activity. Administration of the active L-threo enantiomer of the compound (I), substantially free of its other isomers, would essentially enable a reduction in the dose of drug. Due to the importance of the L-threo enantiomer of the compound (I) as an oral, synthetic norepinephrine precursor, there exists a need to develop an economical and efficient synthetic process for its production.

U.S. Pat. No. 4,562,263 (hereinafter US '263) discloses a process for preparation of droxidopa comprising optical resolution of N-phthaloyl-3-(3,4-methylenedioxyphenyl)serine using optically active amine selected from the group consisting of strychinine, cinconidine, L-norephedrine, S-2-amino-1,1-diphenyl-1-propanol and L-3-hydroxy-3-(4-nitrophenyl)-2-amino-1-propanol to yield L-N-phthaloyl-3-(3,4-methylenedioxyphenyl)serine, reacting the resulting compound with a Lewis acid selected from the group consisting of aluminium trichloride, aluminium tribromide, boron trichloride and boron tribromide to form N-phthaloyl-3-(3,4-dihydroxyphenyl)-serine; which on further deprotection by removal of phthaloyl group with hydrazine to yield L-threo-3-(3,4-dihydroxyphenyl)-serine.

U.S. Pat. No. 3,920,728 (hereinafter US '728) provides a process for the preparation of droxidopa comprising reaction of 3,4-dibenzyloxybenzaldehyde with glycine, followed by treatment with sodium acetate trihydrate and diethylamine to obtain racemic-threo/erythro-3-(3,4-dibenzyloxyphenyl)-serine. Further, treatment of the compound with carbobenzoxy chloride to obtain racemic-threo/erythro-3-(3,4-dibenzyloxyphenyl)-N-carbobenzoxyserine and its treatment with dicyclohexylamine to give racemic-threo-3-(3,4-dibenzyloxyphenyl)-N-carbobenzoxyserinedicyclohexylamine salt, which on treatment with HCl gas in the presence of ethyl acetate yields racemic-threo-3-(3,4-dibenzyloxyphenyl)-N-carbobenzoxyserine. Finally, treatment of the racemic serine compound with (+)-ephedrine to yield (+)-ephedrine salt of L-threo-3-(3,4-dibenzyloxyphenyl)-N-carbobenzoxyserine and hydrolysis of the compound to yield L-threo-3-(3,4-dibenzyloxyphenyl)-N-carbobenzoxyserine; which on subsequent reduction over Pd/C provides L-threo-3-(3,4-dibenzyloxyphenyl)-serine.

The patent EP0024210B1 describes a process for preparation of optically active (D- or L-) threo-3-(3,4-dihydroxyphenyl)serine (Droxidopa) comprising reaction of racemic threo-3-(3,4-dibenzyloxyphenyl)-N-carbobenzoxyserine with a resolving agent, followed by decomposition using hydrochloric acid to yield (−)-3-(3,4-dibenzyloxyphenyl)-N-carbobenzoxyserine.

The published PCT application WO-A-2017/168313 disclosed the treatment of 2-ethoxybenzo[d][1,3]dioxole-5-carbaldehyde (IIIa) with the Ni-complex compound (IIa) in the presence of a metal alkoxide selected from sodium methoxide to obtain intermediate compound (IVa) which is optionally isolated or in-situ hydrolysed by the treatment with an acid selected from hydrochloric acid to obtain salt of droxidopa (I). The salt was treated with a base selected from triethylamine in aqueous medium and the desired product was obtained with more than 99% ee, which is illustrated below:

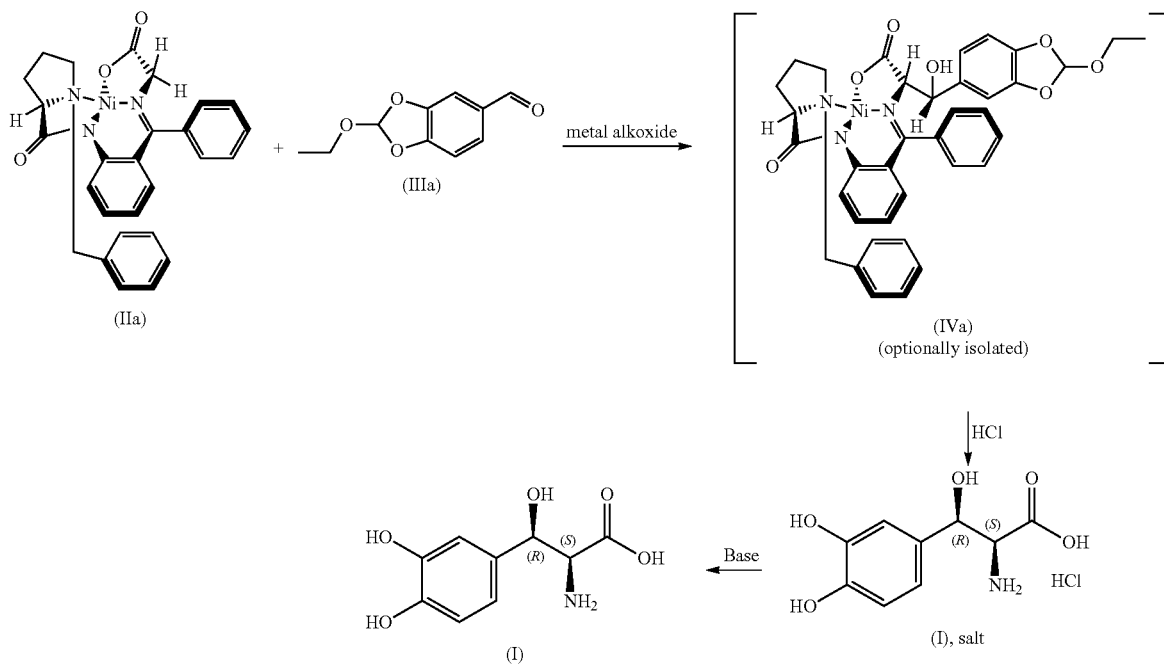

The published PCT application WO-A-2005/085178 disclosed the treatment of 1-hydroxy-1-(3,4-dibenzyloxyphenyl) glycine-Ni-D-2-[N—(N'-benzylprolyl) amino] benzophenone with hydrochloric acid to obtain L-threo-(2S,3R)-3-(3,4-dibenzyloxyphenyl) serine. As indicated, the said compound has both the hydroxyl group protected with benzyl group to form 3,4-dibenzyloxyphenyl compound. The product on subsequent metal catalyzed hydrogenation, predominately using Pd/C under hydrogenation pressure provides Droxidopa.

A general method for the synthesis of enantiomerically pure beta-Hydroxy-alpha-amino acids and serine derivatives is also disclosed in the *J. Chem. Soc. Perkin Trans.* 1, 3143-54 (1993), *J. Am. Chem. Soc.* 107, 4252-59 (1985), *J. Am. Chem. Soc.* 107, 4252-59 (7985), *Journal of fluorine chemistry* 75, 93-101, (1995) and published patent application US 2015/0210667A1.

It is evident from the above discussion that the prior art processes for the preparation of droxidopa involves multiple process steps such as resolution followed by separate deprotection method. The use of resolving agent renders the process costly. Partial recycling of the resolving agent is feasible but such recycling is costly as it requires additional processing and is also associated with waste generation. The undesired enantiomer cannot be recycled and is discarded. The chiral resolution to obtain threo/erythro isomer results into 50% loss of the undesired isomer, which affects the overall yield of the process. Further, the process involves use of complex agents for isomer separation, which also results in <50% of desired isomer. Also, the hydrazine used for the deprotection of phthaloyl group is known to be genotoxic, and thus it is required to remove traces of hydrazine from the final product, droxidopa.

Thus, in view of these drawbacks there is a need to develop an alternative asymmetric synthesis which would provide the desired L-threo isomer in an efficient and more specific manner; and also there was need to develop economical method. The said prior art processes are therefore disadvantageous for commercial manufacturing due to non-feasibility of the reaction process owing to use of genotoxic reagents, and due to the elaborate and tedious nature of the process, providing low yield of the desired isomer.

Inventors of the present invention have developed an improved process which is a simple, efficient and cost-effective process and provides the desired compounds in improved yield and purity and that addresses the problems associated with the processes reported in the prior art. The process of the present invention does not involve use of any toxic and/or costly solvents, also does not involve use of costlier coupling agents and reagents. Moreover, the process does not require repetitive purification steps and column chromatography. Accordingly, the present invention provides a process for the preparation of droxidopa (I), which is simple, efficient, cost effective, environmentally friendly and commercially scalable for large scale operations.

SUMMARY OF THE INVENTION

In one aspect, the present invention relates to an improved process for the preparation of L-threo-(2S,3R)-3-(3,4-dihydroxyphenyl)serine (I) or a salt thereof; comprising recovery and recycling of the by-product compound (V) (as described herein) from the crude compound (I).

In one aspect, the present invention relates to an improved process for the preparation of L-threo-(2S,3R)-3-(3,4-dihydroxyphenyl)serine (I) or a salt thereof; comprising (a) recovery of the by-product compound (V) (as described herein) from the crude compound (I), and (b) recycling and re-use it for the preparation of droxidopa.

In a specific embodiment, the present invention relates to an improved process for the recovery of the by-product compound (V) (as described herein); comprising the steps of suspending the crude compound (I) containing the compound (V) in a solvent, followed by the treatment with an acid.

In another aspect, embodiment, the present invention relates to an improved process for the preparation of pure recovered compound (V) or a salt thereof; comprising purification of the compound (V) or a salt thereof by using water.

DETAILED DESCRIPTION OF THE INVENTION

Accordingly, the present invention relates to an improved process for the preparation of L-threo-(2S,3R)-3-(3,4-dihydroxyphenyl)serine (I) or a salt thereof; comprising recovery and recycling of the by-product compound (V) (as described herein) from the crude compound (I).

For the purpose of the instant invention, the term "crude" in reference to droxidopa as used herein "crude" droxidopa (1) or its salt, in which droxidopa is contaminated with other impurity and by-products. Particularly, the crude droxidopa, as disclosed herein contains the compound of formula (V).

In purview of the present invention, the 'compound (V)' refers to the compound (R)—N-(2-benzoylphenyl)-1-benzylpyrrolidine-2-carboxamide or its salt represented by the following formula,

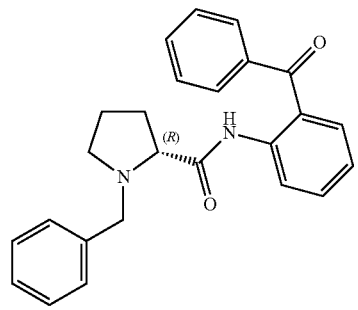

(V)

In one aspect, the present invention relates to an improved process for the preparation of L-threo-(2S,3R)-3-(3,4-dihydroxyphenyl)serine (I) or a salt thereof; comprising (a) recovery of the by-product compound (V) (as described herein) from the crude compound (1), and (b) recycling it for the preparation of droxidopa.

Accordingly, the present invention relates to an improved process for the preparation of L-threo-(2S,3R)-3-(3,4-dihydroxyphenyl)serine (1) or a salt thereof represented by the following formula,

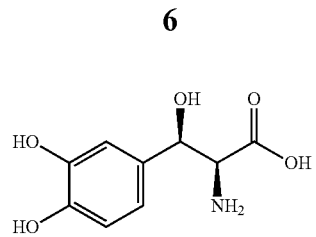

(I)

comprising the steps of,
(a) recovery of the by-product compound (V) or its salt represented by the following formula,

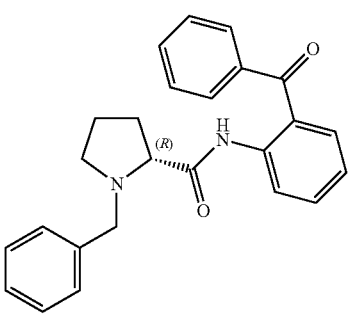

(V)

from the crude compound (I).
(b) recycling the recovered compound (V) for the preparation of droxidopa.

For the purpose of the instant invention, the term as used herein, "recovery" of by-product or its salt, refers to the separation and isolation of the compound from the crude mixture.

In purview of the scope of the instant invention, the by-product precisely refers to the key starting material formed during the course of reaction.

For the purpose of instant invention, the term as used herein, "recycling" of the recovered compound or its salt, refers to the re-use of the separated compound for the preparation of droxidopa (I).

The process of the present invention as per the specific embodiment described above is illustrated in the following Scheme (I), Scheme (I)

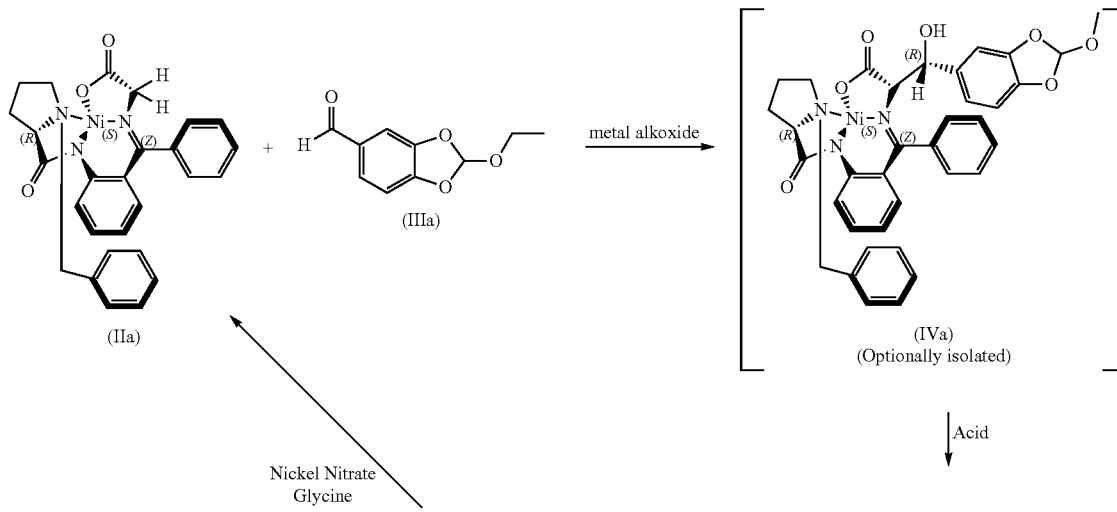

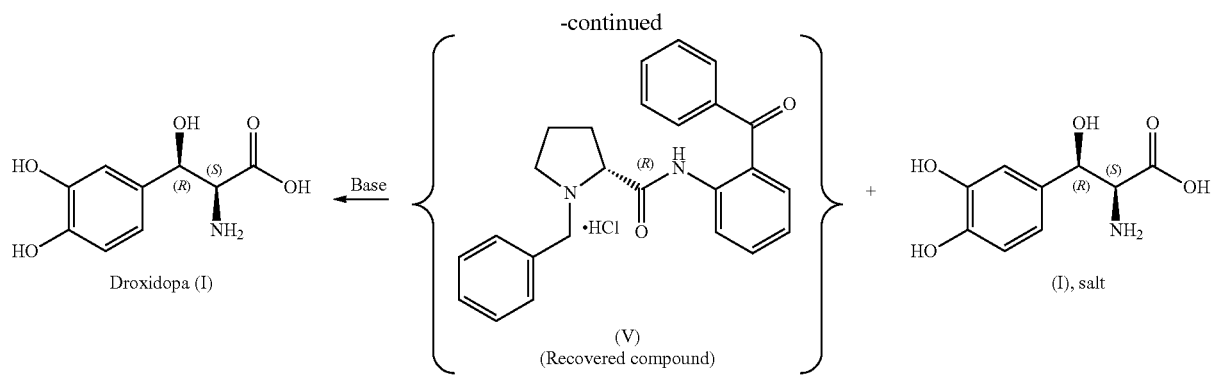

It is evident that, several processes are reported in the prior art for the preparation of droxidopa (I). Hence, the product as compound (I) can be obtained by any of the prior known methods in the art. For instance, considering the process as disclosed in the published PCT application WO-A-2017/168313 for the preparation of droxidopa (I). Similarly, the preparation of compound (IIa) from the compound (V) is well disclosed in the prior art such as published PCT application WO-A-2005/085178.

The metal alkoxide used in the above process (as depicted in the Scheme (I)) is selected from the sodium methoxide, sodium ethoxide, sodium isopropoxide, potassium methoxide, sodium tertiary butoxide, potassium tertiary butoxide, or mixtures thereof.

The acid used in the above process (as depicted in the Scheme (I)) is selected from hydrochloric acid, hydrobromic acid, hydrofluoric acid, nitric acid, sulfuric acid, formic acid, acetic acid, trifluoro acetic acid and phosphoric acid or mixtures thereof.

The base used in the above process (as depicted in the Scheme (I)) is selected from an organic base or an inorganic base such as triethylamine (TEA), N,N-diisopropylethylamine, tripropylamine, pyridine, sodium carbonate, sodium bicarbonate, potassium carbonate, sodium hydroxide, potassium hydroxide, lithium hydroxide, lithium carbonate, sodium bicarbonate, potassium bicarbonate, sodium hydride, or a mixture thereof.

In a specific embodiment, the process for recovery and recycling of the by-product compound (V) comprises the steps of;
(i) suspending the crude compound (I) containing the compound (V) in a solvent,
(ii) adding an acid to the reaction mixture of step (i),
(iii) isolating the compound (V) from the reaction mixture of step (ii),
(iv) optionally, recycling the compound of step (iii) for the synthesis of droxidopa (I)

In an embodiment the 'solvent' is selected from the group consisting of halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; water or a mixture thereof In an embodiment the 'acid' is selected from the group consisting of hydrochloric acid (HCl), hydrobromic acid, hydrofluoric acid, nitric acid, sulfuric acid, formic acid, acetic acid, trifluoro acetic acid and phosphoric acid or mixtures thereof.

In an embodiment the term 'isolating' the product' referred to in any process step from step (iii) corresponds to the isolating the compound using methods that corresponds precipitation, evaporation of solvent, filtration, washing or drying.

In the context of the present invention, the term "optionally" when used in reference to any element; including a process step e.g. recycling the compound (V): it is intended to mean that the recovered subject compound is subsequently re-used, or alternatively, is not re-used. Both alternatives are intended to be within the scope of the present invention.

The process of the present invention as per the specific embodiment described above is illustrated in the following Scheme (II):

Scheme (II)

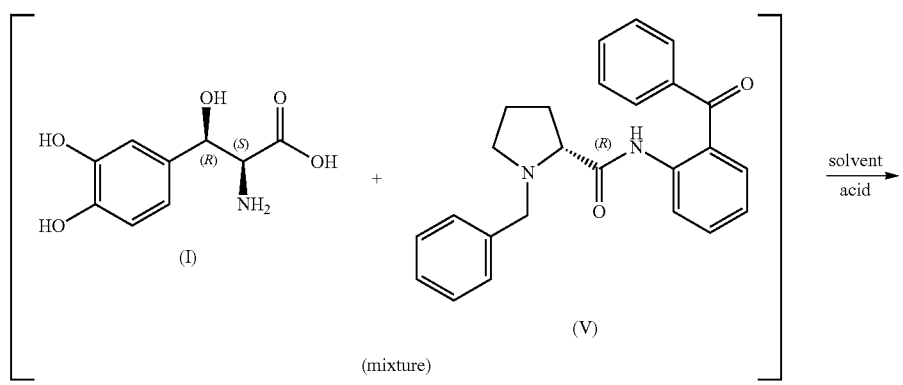

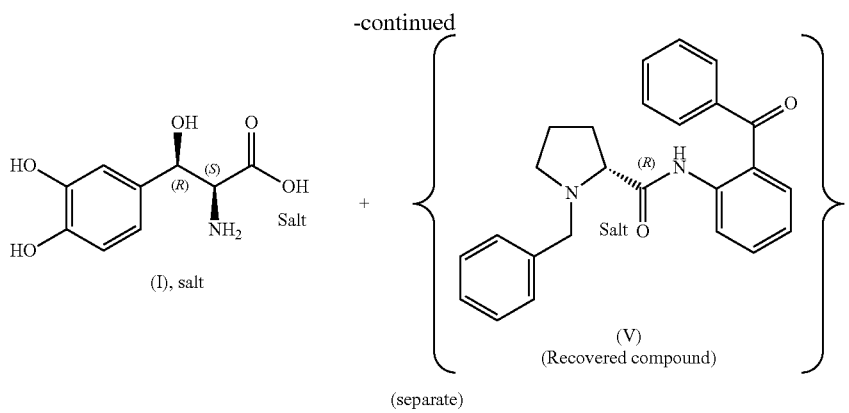

(separate)

The process of the present invention as illustrated in the above Scheme (I) and Scheme (II) comprises dissolving the compound (IIa) and compound (IIIa) in methanol, followed by the addition of metal alkoxide such as sodium methoxide. To the reaction mixture containing the intermediated compound (IVa), was added an acid such as hydrochloric acid. The precipitated recovered compound (V) salt was isolated by filtration and drying with molar yield of more than 98% and with chiral purity more than 99%. The filtrate was further washed with a solvent such as ethyl acetate and the aqueous phase was cooled to −5 to 5° C. The precipitated product droxidopa salt as compound (I) was filtered having HPLC purity more than 98%.

In a further embodiment, the recovered compound (V) is recycled by the process comprising converting the recovered compound (V) to the metal complex compound (IIa) and subsequently transforming to the droxidopa (I).

The recovered compound (V) can be converted into the metal complex compound (IIa) by any of the process known in the art. For instance, the recovered compound (V) is reacted with metal nitrate such as nickel nitrate and glycine to obtain the Nickel complex compound (IIa); which is illustrated in the following Scheme (III);

Scheme (III)

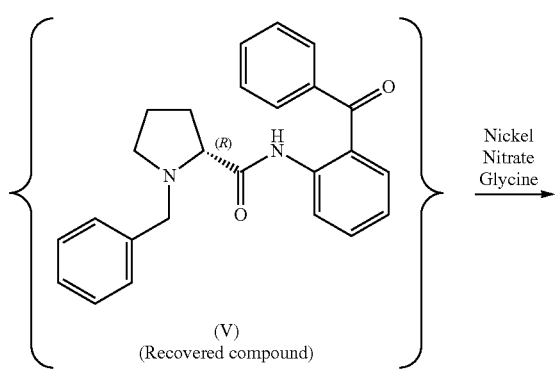

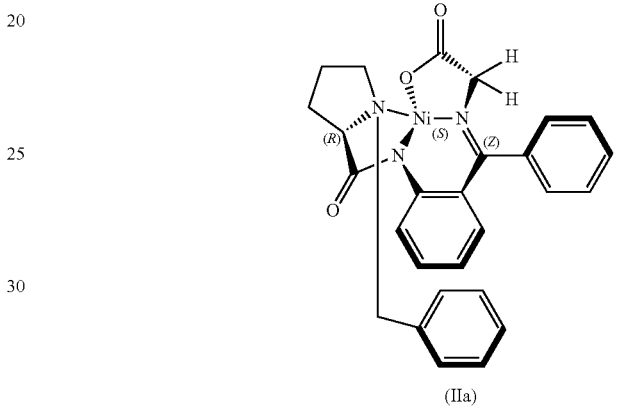

In an embodiment, the present invention relates to an improved process for the preparation of pure recovered compound (V) or a salt thereof: comprising purification of the compound (V) or a salt thereof by using water.

For the purpose of instant invention, the term as used herein "pure" recovered compound (V) or its salt, in which compound (V) has chiral purity of more than about 99% ee. Particularly, the pure recovered compound (V), as disclosed herein, has chiral purity of more than about 99.5%, more specifically chiral purity of more than about 99.0%, still more specifically chiral purity of more than about 99.9% ee.

In an embodiment, the pure recovered compound (V) obtained after purification using water has chiral purity of more than about 99% and purity by HPLC more than about 99.9%.

In a specific embodiment, the process for the preparation of pure recovered compound (V) or a salt comprising the steps of;

(1) suspending recovered compound (V) or its salt in water,
(2) stirring the reaction mixture of step (1) at lower temperature.
(3) isolating the desired product as pure recovered compound (V) or its salt.

The term 'lower temperature' referred to in the step (2) of the above process corresponds to the temperature ranging from 25° C. to 35° C.

The term 'isolating' referred to in the step (3) of the above process corresponds to the steps involving filtration, washing and/or drying.

The inventors of the process of the instant invention observed that the pure recovered compound (V) obtained after purification using water has purity of more than about 99% by HPLC.

The following Table-1 indicated purity of recovered compound (V) obtained by the process of the instant invention:

TABLE 1

| Sample | Purity of recovered compound (V) after purification using water |
|---|---|
| Sample 1 | 99.79% |
| Sample 2 | 99.86% |
| Sample 3 | 99.93% |
| Sample 4 | 99.43% |

For the purpose of instant invention, the pure droxidopa (I) or its salt, obtained by the process of instant invention has purity of more than about 98% by HPLC. Particularly, the pure droxidopa, as disclosed herein, has purity of more than about 99% by HPLC, more specifically purity of more than about 99.5% by HPLC, still more specifically purity of more than about 99.9% by HPLC.

In an embodiment, the pure droxidopa (or its salt obtained by the process of instant invention has purity of more than about 99.9% by HPLC.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

The product droxidopa (I) can be obtained by any of the prior known methods in the art. For the purpose of the instant invention, the process as disclosed in the published PCT application WO-A-2017/168313 has been adopted.

Reference Example-1: Preparation of Nickel Complex (IVa)

Charged 300 mL of methanol in a flask followed by the addition of Nickel complex (IIa) (100 g) at temperature of about 25-30° C. To the stirring solution was added 120 mL of 25% Sodium methoxide solution and (40.9 g) aldehyde compound (IIIa). The reaction mixture was stirred for about 1 hour and quenched in acetic acid: water mixture (200 mL of 20% acetic acid & 1000 mL of demineralized (DM) water). The reaction mixture was filtered and solid obtained was washed with 300 mL of DM water to obtain desired product (HPLC purity: 83.4%).

Reference Example-2: Preparation of L-threo-(2S, 3R)-3-(3.4-dihydroxyphenyl)serine (I)

Charged 300 mL of methanol in a flask followed by the addition of Nickel complex (IVa) (30 g) at temperature of about 25-30° C. To the stirring solution was added (75 mL) of 5N HCl and the reaction mixture was heated to 40° C. After 2 hours, the reaction was cooled to 25-30° C. and concentrated under vacuum. The residue of crude Droxidopa hydrochloride salt was converted to its free base by adjusting the pH to 7.5-8.5 with 25% triethylamine in methanol solution in 5 volumes (V) (w.r.t weight. of HCl salt) DM water medium for about 1 hour. The solid was filtered and washed with (2×4V) of DM water and (2×7V) of methanol to obtain desired product. (Yield 76%, chiral purity 99.65% (ee)).

Reference Example-3: Preparation of L-threo-(2S, 3R)-3-(3.4-dihydroxyphenyl)serine (I) Hydrochloride Charged 420 mL of methanol in a flask followed by the addition of sodium methoxide solution (55 mL), Nickel complex (IIa) (100 g) and aldehyde compound (IIIa). The reaction mixture was stirred at temperature of about 15-20° C. for about 1 hour. The reaction mixture was further cooled to about 10° C. temperature; to the reaction mixture was added concentrated hydrochloric acid (100 mL) and stirred for 3 hours at elevated temperature of about 40° C. The reaction mixture was filtered and washed with aqueous HCl. The aqueous filtrate was separately treated with methylene dichloride (350 mL) and ethyl acetate (350 mL) respectively. The separated aqueous layer was cooled to −5 to 5° C. of temperature and stirred for about 3 hour to obtain solid precipitate of L-threo-(2S,3R)-3-(3.4-dihydroxyphenyl)serine (I) HCl salt. The obtained (I) HCl salt was recrystallized from isopropyl alcohol (Yield: 85%, chiral purity 99.99% ee).

Reference Example-4: Preparation of L-threo-(2S, 3R)-3-(3.4-dihydroxyphenyl)serine (I)

The Droxidopa hydrochloride salt (100 g) was converted to free base by adjusting the pH to 7.5-8.5 of its aqueous solution using triethylamine (150 mL) in methanol (150 mL) as solution. The solid was filtered and washed with water (100 mL) followed by washing with methanol (100 mL) to obtain desired product. (Yield: 65 g (76.5%), chiral purity 99.99% ee).

Example-A: Recovery of the (R)—N-(2-benzoylphenyl)-1-benzylpyrrolidine-2-carboxamide (V) hydrochloride Charged 500 mL of methanol in a flask followed by the addition of sodium methoxide solution in methanol (55 mL), Nickel complex (IIa) (100 g) and aldehyde compound (IIIa). The reaction mixture was stirred at temperature of about 15-20° C. for about 1 hour. The reaction mixture was further cooled to about 10° C. temperature; to the reaction mixture was added concentrated hydrochloric acid (100 mL) and stirred for 3 hours at elevated temperature of about 40° C. The reaction mixture was concentrated to the reaction mass upto 2 Volume and to the reaction mixture was added 1500 mL of dilute hydrochloric acid. The mixture was stirred for 15 min at temperature of about 25-30° C. The solid (compound (V)) was filtered and washed with dilute hydrochloric acid (100 mL). The recovered by-product (compound (V)) was dried 45-50° C. temperature. (Yield: 83 g. purity by HPLC 99.5% and chiral purity 99.9% ee).

The separated filtrate was treated with methylene dichloride (350 mL) and ethyl acetate (350 mL) respectively. The separated aqueous layer was cooled to −5 to 5° C. of temperature and stirred for about 3 hour to obtain solid precipitate of L-threo-(2S,3R)-3-(3.4-dihydroxyphenyl)serine (1) HC salt. The obtained (I) HCl salt was recrystallized from isopropyl alcohol (Yield: 40 g, chiral purity 99.99% ee, purity by HPLC: 98%).

The pure (I) HCl salt was further converted to its free base, that is L-threo-(2S,3R)-3-(3.4-dihydroxyphenyl)serine (I) (Droxidopa) using the method disclosed under reference example-4.

Example-B: Purification of Recovered (R)—N-(2-Benzoylphenyl)-1-benzylpyrrolidine-2-Carboxamide (V) Hydrochloride Charged 2.4 L of water in a flask followed by the addition of 400 g of recovered compound (V) hydrochloride at room temperature. The reaction mixture was stirred for 2 hours at temperature of about 25° C. to 30° C. The solid was filtered and washed with 1.6 L of water. The obtained solid was dried to give desired pure compound (V) (yield: 320 g, chiral purity 100%, purity by HPLC: 99.93%).

We claim:

1. A process for the preparation of pure Droxidopa (I) or its salt of the following formula;

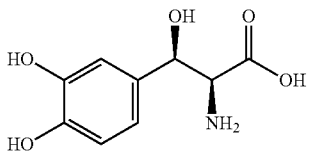

comprising the steps of,
(a) recovery of the by-product compound (V) or its salt of the following formula,

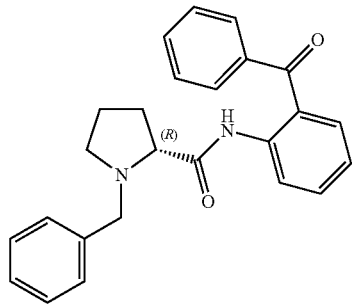

from the crude compound (I), comprising the steps of;
(i) suspending the crude compound (I) containing the compound (V) in a solvent,
(ii) adding an acid to the reaction mixture of step (i),
(iii) isolating the compound (V) from the reaction mixture of step (ii),
(b) optionally, recycling the recovered compound IV) obtained from step (a) for the preparation of droxidopa.

2. The process according to claim 1, wherein the solvent used in step (i) is selected from the group consisting of halogenated solvent, alcoholic solvent, ether solvent, ketone solvent, aromatic solvent, an aprotic solvent such as acetonitrile, N,N-dimethyl formamide (DMF), N,N-dimethyl acetamide, dimethyl sulfoxide (DMSO) and N-methylpyrrolidone (NMP), water or a mixture thereof.

3. The process according to claim 1, wherein the acid used in step (ii) is selected from the group consisting of hydrochloric acid (HCl), hydrobromic acid, hydrofluoric acid, nitric acid, sulfuric acid, formic acid, acetic acid, trifluoro acetic acid and phosphoric acid or mixtures thereof.

4. The process according to claim 1, wherein the obtained product pure droxidopa (I) or its salt, has a purity of more than about 98% by HPLC.

5. The process according to claim 1, wherein the obtained product pure droxidopa (I) or its salt, has a purity of more than about 99.9% by HPLC.

6. The process according to claim 1, wherein the recovered compound (V) or a salt is purified by method comprising the steps of;
(1) suspending recovered compound (V) or its salt in water,
(2) stirring the reaction mixture of step (I) at lower temperature,
(3) isolating the desired product as pure recovered compound (V) or its salt.

7. The process according to claim 6, wherein the lower temperature of step (2) corresponds to the temperature ranging from 25° C. to 35° C.

8. The process according to claim 6, wherein the recovered pure compound (V) or its salt has a chiral purity of more than about 99.9% ee.

* * * * *